United States Patent [19]

Jan et al.

[11] Patent Number: 5,196,603
[45] Date of Patent: Mar. 23, 1993

[54] PROCESS FOR DECOMPOSING PEROXIDE IMPURITIES IN A TERITARY BUTYL ALCOHOL FEEDSTOCK USING AN IRON (II) COMPOUND

[75] Inventors: Chwu-Ching Jan, Elk Grove Village; Thomas P. Malloy, Lake Zurich, both of Ill.

[73] Assignee: UOP, Des Plaines, Ill.

[21] Appl. No.: 828,252

[22] Filed: Jan. 30, 1992

Related U.S. Application Data

[62] Division of Ser. No. 653,921, Feb. 12, 1991, Pat. No. 5,124,492.

[51] Int. Cl.⁵ .................... C07C 29/88; C07C 29/132; C07C 31/12
[52] U.S. Cl. .................................. 568/917; 568/914; 568/909.8
[58] Field of Search ............. 568/909.8, 917, 914

[56] References Cited

U.S. PATENT DOCUMENTS

| | | | |
|---|---|---|---|
| 2,628,986 | 2/1953 | Wallace et al. | 568/917 |
| 2,792,344 | 5/1957 | Tidwell | 568/917 |
| 2,993,072 | 7/1961 | Chiusoli et al. | 260/537 |
| 3,373,180 | 3/1963 | Glass et al. | 568/917 |
| 3,470,239 | 9/1965 | Russell | 260/486 |
| 3,747,151 | 10/1969 | Grane | 260/643 |
| 4,547,598 | 10/1985 | Sanderson et al. | 568/922 |
| 4,551,553 | 11/1985 | Taylor et al. | 568/311 |
| 4,704,482 | 11/1987 | Sanderson et al. | 568/922 |
| 4,705,903 | 11/1987 | Sanderson et al. | 568/922 |
| 4,742,179 | 11/1988 | Sanderson et al. | 568/913 |
| 4,873,380 | 10/1989 | Sanderson et al. | 568/914 |
| 4,922,034 | 5/1990 | Sanderson et al. | 568/909.8 |
| 4,922,035 | 5/1990 | Sanderson et al. | 568/914 |
| 4,922,036 | 5/1990 | Sanderson et al. | 568/914 |
| 4,922,602 | 5/1990 | Sanderson et al. | 568/909.8 |
| 4,978,799 | 12/1990 | Sanderson et al. | 568/909.8 |
| 5,025,112 | 6/1991 | Sanderson et al. | 585/852 |
| 5,025,113 | 6/1991 | Sanderson et al. | 568/909.8 |
| 5,120,886 | 6/1992 | Lyons et al. | 568/909.8 |
| 5,124,492 | 6/1992 | Jon et al. | 568/909.8 |

*Primary Examiner*—Joseph E. Evans
*Attorney, Agent, or Firm*—Thomas K. McBride; Eugene I. Snyder; Frank S. Molinaro

[57] ABSTRACT

This invention relates to a process for removing impurities contained in a teritary butyl alcohol feedstock. The process involves contacting the feedstock with an iron (II) compound such as iron (II) chloride, under an inert atmosphere at elevated pressures and temperatures for a time sufficient to reduce the peroxides to alcohols and oxidize the iron (II) to iron (III). The iron (II) compound is added in a homogeneous phase which, after reaction has occurred, gives a mixture of the treated teritary butyl alcohol, iron (III) compound and any residual iron (II) compound. The iron (III) and any iron (II) compounds are separated from the product by contacting the mixture with a cation exchange column.

4 Claims, No Drawings

PROCESS FOR DECOMPOSING PEROXIDE IMPURITIES IN A TERITARY BUTYL ALCOHOL FEEDSTOCK USING AN IRON (II) COMPOUND

CROSS REFERENCE TO RELATED APPLICATION

This application is a division of copending application U.S. Ser. No. 07/653,921 filed on Feb. 12, 1991, now U.S. Pat. No. 5,124,492.

FIELD OF THE INVENTION

This invention relates to a process for purifying a tertiary butyl alcohol feedstock which contains peroxides such as tertiary butyl hydroperoxide and di-tertiary butyl peroxide. In particular this invention relates to a method of decomposing the peroxides contained in the tertiary butyl alcohol feedstock by contacting the feedstock with an iron (II) compound. The process can be carried out in a homogeneous mode, where the compound is dissolved in the feedstock followed by a separation step where the compound/feedstock is contacted with a resin to remove the iron. Alternatively, the feedstock may be contacted with an iron (II) compound which is deposited on a solid support thereby eliminating the separation step.

BACKGROUND OF THE INVENTION

When tertiary butyl hydroperoxide is reacted with propylene to form propylene oxide, tertiary butyl alcohol is the main byproduct. The tertiary butyl alcohol is usually separated from the propylene oxide by distillation, but it will contain peroxide impurities such as tertiary butyl hydroperoxide and di-tertiary butyl peroxide. The tertiary butyl alcohol may be used as a gasoline additive, or it may be dehydrated to make isobutylene which can then be used to make methyl-t-butyl ether. The process of making isobutylene from tertiary butyl alcohol involves the use of a dehydration catalyst which is usually a metal ion which has been exchanged onto a resin support. However, the peroxides which are present in the tertiary butyl alcohol can destroy the dehydration catalyst and therefore it is necessary to reduce the amount of peroxide impurities to a few ppm, i.e., less than 20 ppm.

The prior art has addressed the problem of decomposition of peroxides in tertiary butyl alcohol in regard to use of tertiary butyl alcohol as a gasoline additive. For example, U.S. Pat. No. 3,474,151 discloses a process for decomposing peroxides in tertiary butyl alcohol by heating the tertiary butyl alcohol at a temperature of 375° F. to 475° F. Other references disclose catalytic methods for decomposing peroxide impurities in tertiary butyl alcohol feedstocks. These references include the following: 1) U.S. Pat. No. 4,551,553 which discloses a homogeneous process of decomposing hydroperoxides using a catalyst which is a chromium and ruthenium salt; 2) U.S. Pat. No. 4,873,380 which discloses the use of a catalyst which contains oxides of nickel, copper, chromium and barium to decompose tertiary butyl hydroperoxide and di-tertiary butyl peroxide in a tertiary butyl alcohol feedstock; 3) U.S. Pat. No. 4,742,179 which discloses the decomposition of peroxides in a tertiary butyl alcohol feedstock using a catalyst which consists of one or more of a group VIB or VIII metal which has been base treated and optionally contains a Group IB promoter; 4) U.S. Pat. No. 4,705,903 which discloses the decomposition of peroxides using a catalyst composed of iron, copper, chromia and cobalt; 5) U.S. Pat. No. 4,704,482 which discloses the decomposition of peroxides using a catalyst containing nickel, copper, chromia and iron oxide either unsupported or supported on silica; and 6) U.S. Pat. No. 4,547,598 which discloses a method of decomposing hydroperoxides using a catalyst which is cobalt borate or cobalt borate on titanium dioxide.

In contrast to this prior art, the instant invention reduces or decomposes tertiary butyl hydroperoxide and di-tertiary butyl peroxides to alcohols using an iron (II) compound. During the reaction the iron (II) is oxidized to iron (III) while the peroxides are reduced to the alcohol. The iron (II) compound may be used in a homogeneous phase, that is by using an iron (II) compound which is soluble in the tertiary butyl alcohol or by depositing the iron (II) compound onto a solid support such as a resin or a zeolite. By using only an iron (II) compound, applicants have been able to produce a tertiary butyl alcohol product that contains about 20 ppm of total peroxides. There is nothing in the prior art that suggests that iron (II) could be effective in decomposing tertiary butyl hydroperoxide and especially di-tertiary butyl peroxide which is difficult to decompose. Accordingly, applicants have met a need in the industry for a tertiary butyl alcohol feedstock which contains less than 20 ppm of total peroxide impurities so that the tertiary butyl alcohol may be dehydrated and then used to make methyl-t-butyl ether.

What is also surprising about applicants' invention is that the iron (II) compound is able to reduce the di-tertiary butyl peroxide. It is well known that di-tertiary butyl peroxide is one of the hardest peroxides to decompose and thus it is extremely surprising that an iron (II) compound can effectively and virtually completely reduce or decompose all the di-tertiary butyl peroxides contained in the tertiary butyl alcohol feedstock.

SUMMARY OF THE INVENTION

As stated, this invention relates to processes for decomposing peroxide impurities contained in a tertiary butyl alcohol feedstock. Accordingly, one embodiment of the invention is a process for removing peroxide impurities from a tertiary butyl alcohol feedstock to afford a tertiary butyl alcohol product containing less than 20 ppm of peroxides, comprising contacting the feedstock with an iron (II) compound at reduction conditions to reduce the peroxides to alcohols and oxidize the iron (II) to iron (III) thereby providing a mixture of the treated tertiary butyl alcohol, iron (III) compound, and any residual iron (II) compound and flowing the mixture over a cation exchange column to separate the iron compounds from the tertiary butyl alcohol and recover the tertiary butyl alcohol product.

This and other objects and embodiments of the invention will become more apparent after a more detailed description of the invention.

DETAILED DESCRIPTION OF THE INVENTION

As stated this invention relates to processes for reducing peroxide impurities contained in a tertiary butyl alcohol feedstock. One source of the peroxide contaminated tertiary butyl alcohol feedstock is the production of propylene oxide, in which the tertiary butyl alcohol is a byproduct. The overall process involves taking isobutane and reacting it with molecular oxygen to give as the principal products tertiary butyl alcohol and tertiary butyl hydroperoxide. However, minor amounts of other peroxides including di-tertiary butyl peroxide, allyl tertiary butyl peroxide, etc. are also formed. The tertiary butyl hydroperoxide, which also contains the other peroxides, is now reacted with propylene to yield propylene oxide and tertiary butyl alcohol. When the tertiary butyl alcohol is separated from the propylene oxide, the alcohol will contain all the peroxide impurities still present in the mixture. Of the peroxides which may be present in the tertiary butyl alcohol, the one found in greatest concentration is di-tertiary butyl peroxide. The process of this invention is, therefore, particularly suited for removing di-tertiary butyl peroxides. Although the total amount of peroxides is usually small, from about 100 ppm to about 1.5 weight percent, it is large enough to make the tertiary butyl alcohol unfit for use in the preparation of methyl-t-butyl ether. That is, the peroxides destroy the dehydration catalyst which is used to convert the tertiary butyl alcohol to isobutylene. Accordingly, the peroxides must be removed or decomposed such that the total concentration of peroxides is less than 20 ppm.

The process of the instant invention can be used to remove peroxide impurities from any tertiary butyl alcohol feedstock containing greater than about 20 ppm of peroxides. The process involves reducing or decomposing the peroxides to the corresponding alcohols. In order to accomplish this, the tertiary butyl alcohol feedstock which contains the peroxide impurities is contacted with an iron (II) compound. The iron (II) compound reacts with the peroxide to reduce the peroxide to the alcohol while the iron (II) is oxidized to iron (III). The reaction is stoichiometric and thus the iron (II) compound is a reducing agent and not a catalyst.

The iron (II) compound, which acts as a reducing agent, may be either added to the feedstock or be deposited on a solid support. If the compound is added to the feedstock, it should be present in a soluble form so that it is intimately mixed with the tertiary butyl alcohol feedstock. Illustrative of the iron (II) compounds which can be used in the invention are iron chloride, iron acetate, iron sulfate, and iron nitrate. These compounds may be added to the tertiary butyl alcohol in a concentration from about 0.1 to about 1.5 and preferably from about 0.3 to about 0.7 weight percent of the feedstock. The desired iron (II) compound may be added directly to the tertiary butyl alcohol or it may be dissolved in another solvent and the resulting solution added to the tertiary butyl alcohol. Examples of solvents in which the iron (II) compounds may be dissolved are water, ethyl alcohol, and acetone.

Having mixed or contacted the tertiary butyl alcohol feedstock with the desired iron (II) compound, the resultant mixture is now heated at a temperature of about 80° to about 200° C. and a pressure sufficient to maintain the mixture in a liquid phase. Typically this means a pressure of 1378 kPa (200 psi) to about 6894 kPa (1000 psi) depending on the reaction temperature. Higher pressures of up to 13,789 kPa (2000 psi) can be used, but there is no particular advantage in using such higher pressures. The tertiary butyl alcohol is contacted with the desired iron (II) compound for a time sufficient to decompose the peroxides contained in the feedstock, which generally is from about 1 to about 6 hours. It is also necessary that the reaction be carried out under a non-oxidizing or inert atmosphere, since the iron (II) compounds which act as the reducing agents are easily oxidized under the presence of oxygen. Examples of inert atmospheres are nitrogen, argon, helium, etc. Therefore, the pressure stated above represents the pressure of the particular inert or non-oxidizing gas.

Having reduced the peroxides to alcohols, one obtains a mixture of the treated tertiary butyl alcohol, the oxidized iron compound, i.e., iron (III) compound and any residual iron (II) compound. It is therefore necessary to remove the iron (III) compound and any iron (II) compound from the tertiary butyl alcohol product. This can be accomplished by flowing the mixture over a cation exchange column to remove the iron cations which are present in the mixture. In order to ensure adequate contact time between the mixture and the column, the mixture is flowed through the column at a liquid hourly space velocity of about 1.0 to about 2.0 $hr^{-1}$. Any cation exchange resins well known in the art may be used to remove the iron. These include strong acid and weak acid resins. A strong acid resin is one that commonly contains sulfonic acid groups attached to a styrenic backbone, whereas a weak-acid resin is one that contains a carboxylic acid functional group attached to a backbone. Although both strong and weak acid resins can be used to remove the iron, it is preferred to use a strong acid resin. If desired, the effluent from the cation exchange column may additionally be flowed over an anion exchange column to remove any unwanted anions present in said mixture. Having removed the undesirable iron cations and any unwanted anions, a tertiary butyl alcohol product is recovered which contains less than 20 ppm of total peroxide impurities.

An alternative method of carrying out the process of the invention is to deposit the iron (II) compound onto a solid support. The supports which may be used in the practice of this invention are selected from the group consisting of weakly acidic resins, amorphous and crystalline silica-aluminas, natural and synthetic clays and zeolites. When the iron (II) compound is deposited on the support it is desirable that it be present in a concentration from about 2 to about 10 weight percent and preferably from about 2 to about 4 weight percent of the support. The conditions necessary to carry out the reduction of the peroxides when a supported iron (II) compound is used are generally the same as when a homogeneous iron (II) compound is used and are described above. The only difference is that the process may be carried out either in a batch or a continuous flow process with a continuous flow being preferred. When the process is carried out in a continuous mode it is necessary that the tertiary butyl alcohol feedstock be flowed through the supported iron (II) column at a liquid hourly space velocity (LHSV) from about 1.0 to about 2.0 $hr^{-1}$ in order to ensure that the tertiary butyl alcohol feedstock is in contact with the iron (II) compound for a sufficient time to reduce the peroxides to alcohols. This flow rate ensures adequate contact time such that a tertiary butyl alcohol product with less than 20 ppm of peroxide impurities is obtained.

When the supported iron (II) has substantially been converted to iron (III), the iron (III) can be regenerated by contacting the supported iron (III) compound with an appropriate reducing agent such as sodium thiosulfite, sulfur dioxide, $HNO_2$, HI or other reducing agents well known in the art. If the decomposition process is run in a continuous manner, the regeneration may be carried out by using a swing bed arrangement whereby when one bed or column is deactivated, that bed is taken out and regenerated, while a fresh bed of iron (II) is brought on stream.

The following examples are presented in illustration of this invention and are not intended as undue limitations on the generally broad scope of the invention as set out in the appended claims.

EXAMPLE 1

To samples of tertiary butyl alcohol there were added various amounts of di-tertiary butyl peroxide. Each sample was treated by adding 150 g of t-butyl alcohol to an aqueous solution consisting of 3 g of $FeCl_2.4H_2O$, and 12 g of distilled water. The mixtures were heated in an autoclave to 80° C. or 25° C., with stirring, under a nitrogen pressure of 5516 kPa (800 psi) for the times indicated in Table 1. The results of these experiments are presented in Table 1.

TABLE 1

DECOMPOSITION OF DI-TERTIARY BUTYL PEROXIDE BY Fe(II)

| Peroxide Conc (ppm) | | Fe(II) | Conditions | % Decomposition |
|---|---|---|---|---|
| Initial | Final | | | |
| 5470 | 50 | Y | 80° C., 1 hr | 99.08 |
| 5470 | 5254 | Y | 25° C., 1 day | 3.94 |
| 5000 | 4968 | N | 80° C., 1 hr | 0.64 |
| 1203 | 19 | Y | 80° C., 1 hr | 98.42 |
| 258 | 18 | Y | 80° C., 1 hr | 93.02 |

The data presented in Table 1 show that iron (II) chloride is able to decompose as much as 99% of the di-tertiary butyl peroxide present in a t-butyl alcohol solution. A high conversion of peroxide to alcohol is obtained regardless of the initial peroxide concentration. The data further indicate that very little decomposition takes place at 25° C. even after one day of contact. Also, no decomposition occurs when there is no iron (II) present in the alcohol.

Clearly, using this process one can obtain a t-butyl alcohol product with less than 20 ppm of peroxide.

EXAMPLE 2

The following procedure was used to deposit iron (II) chloride onto the following supports:
1) Chelex 100-a styrene divinylbenzene copolymer resin containing paired iminodiacetate ions. Obtained from Bio-Rad.
2) Bio-Rex 70-a macroreticular acrylic polymer resin containing carboxylic acid exchange groups. Obtained from Bio-Rad.
3) 13X-Zeolite in the shape of ⅛" sphere and obtained from UOP In a nitrogen dry box, 4.7 g of $FeCl_2.4H_2O$ were placed in a beaker and to it there were added 200 mL of water that had been degassed with nitrogen. This solution was added to 40 g of the desired support in a 600 mL beaker. This mixture was stirred for one-half hour and then the liquid decanted. The support was washed with a total of 600 mL of degassed water in three batches. Finally, the solid support was washed with 200 mL of degassed ethanol.

About 40 g of the supported $Fe(II)Cl_2$ was mixed with 30 g of t-butyl alcohol containing various amounts of di-tertiary butyl peroxide. This mixture was heated up to 80° C. for 4 hours in an autoclave under a nitrogen pressure of 5516 kPa (800 psi). The results of these experiments are presented in Table 2.

TABLE 2

DECOMPOSITION OF DI-TERTIARY BUTYL PEROXIDE BY SUPPORTED Fe(II)

| Peroxide Conc (ppm) | | Support Type | % Decomposition |
|---|---|---|---|
| Initial | Final | | |
| 8800 | 2700 | Bio-Rex 70 | 69.32 |
| 8300 | 3300 | 13X | 60.24 |
| 13000 | 6700 | Chelex 100 | 48.46 |

The results presented in Table 2 show that a supported Fe(II) compound is capable of reducing or decomposing di-tertiary butyl peroxide to the alcohol. Higher temperatures and/or longer times would increase the conversion and result in an acceptable t-butyl alcohol product.

We claim as our invention:

1. A process for removing peroxide impurities from a tertiary butyl alcohol feedstock to afford a tertiary butyl alcohol product containing less than 20 ppm of peroxides, comprising contacting the feedstock with an iron (II) compound at reduction conditions to reduce the peroxides to alcohols and oxidize the iron (II) to iron (III) thereby providing a mixture of the treated tertiary butyl alcohol, iron (III) compound, and any residual iron (II) compound and flowing the mixture over a cation exchange column to separate the iron compounds from the tertiary butyl alcohol and recover the tertiary butyl alcohol product.

2. The process of claim 1 where the iron (II) compound is selected from the group consisting of iron chloride, iron sulfate, iron acetate, and iron nitrate.

3. The process of claim 1 where the iron (II) compound is present in a concentration from about 0.1 to about 1.5 weight percent of the feedstock.

4. The process of claim 1 where the reduction conditions are a temperature of about 80° to about 200° C., a pressure of about 1378 to about 6894 kPa, a time of about 1 to about 6 hours and an inert atmosphere.

* * * * *